(12) United States Patent
Durcan

(10) Patent No.: US 7,105,013 B2
(45) Date of Patent: Sep. 12, 2006

(54) PROTECTIVE SLEEVE ASSEMBLY FOR A BALLOON CATHETER

(75) Inventor: Jonathan P. Durcan, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 510 days.

(21) Appl. No.: 10/261,393

(22) Filed: Sep. 30, 2002

(65) Prior Publication Data
US 2004/0093005 A1 May 13, 2004

(51) Int. Cl.
*A61F 2/06* (2006.01)
(52) U.S. Cl. .................................... 623/1.11
(58) Field of Classification Search ........ 606/190–198, 606/108; 623/1.11, 1.12; 604/96.01, 101.01
See application file for complete search history.

(56) References Cited

U.S. PATENT DOCUMENTS

| | | | |
|---|---|---|---|
| 4,540,404 A | 9/1985 | Wolvek | |
| 4,710,181 A | 12/1987 | Fuqua | |
| 4,738,666 A | 4/1988 | Fuqua | |
| 5,033,007 A | 7/1991 | Kameda | |
| 5,066,298 A | 11/1991 | Hess | |
| 5,116,318 A | 5/1992 | Hillstead | |
| 5,147,302 A | 9/1992 | Euteneuer et al. | |
| 5,352,236 A | 10/1994 | Jung et al. | |
| 5,417,707 A | 5/1995 | Parkola | |
| 5,425,710 A | 6/1995 | Khair et al. | |
| 5,817,100 A * | 10/1998 | Igaki ......................... | 606/194 |
| 5,824,041 A * | 10/1998 | Lenker et al. ............... | 606/195 |
| 5,868,707 A | 2/1999 | Williams et al. | |
| 5,873,880 A | 2/1999 | Williams et al. | |
| 5,893,868 A | 4/1999 | Hanson et al. | |
| 5,964,016 A | 10/1999 | Ito et al. | |
| 6,143,016 A | 11/2000 | Bleam et al. | |
| 6,152,944 A | 11/2000 | Holman et al. | |
| 6,283,743 B1 | 9/2001 | Traxler et al. | |
| 6,287,291 B1 | 9/2001 | Bigus et al. | |
| 6,416,529 B1 | 7/2002 | Holman et al. | |

* cited by examiner

Primary Examiner—Kevin T. Truong
(74) Attorney, Agent, or Firm—Fulwider Patton LLP

(57) ABSTRACT

A protector sleeve assembly for a balloon catheter, configured for being removably disposed on at least a section of the catheter and preferably on at least the catheter noninflated balloon prior to introduction of the catheter in a patient's lumen, including a radially collapsible inner sleeve, and an outer sleeve with a tapered section. The inner sleeve has a relaxed configuration with an inner diameter greater than the outer diameter of the noninflated balloon, and a collapsed configuration with an inner diameter less than the relaxed inner diameter. The outer sleeve is slidably positioned on at least a portion of the inner sleeve and has a tapered first section with an inner diameter tapering towards a nontapered second section, the nontapered second section having a substantially uniform inner diameter less than an outer diameter of the relaxed inner sleeve and configured to hold the inner sleeve in the collapsed configuration.

34 Claims, 3 Drawing Sheets

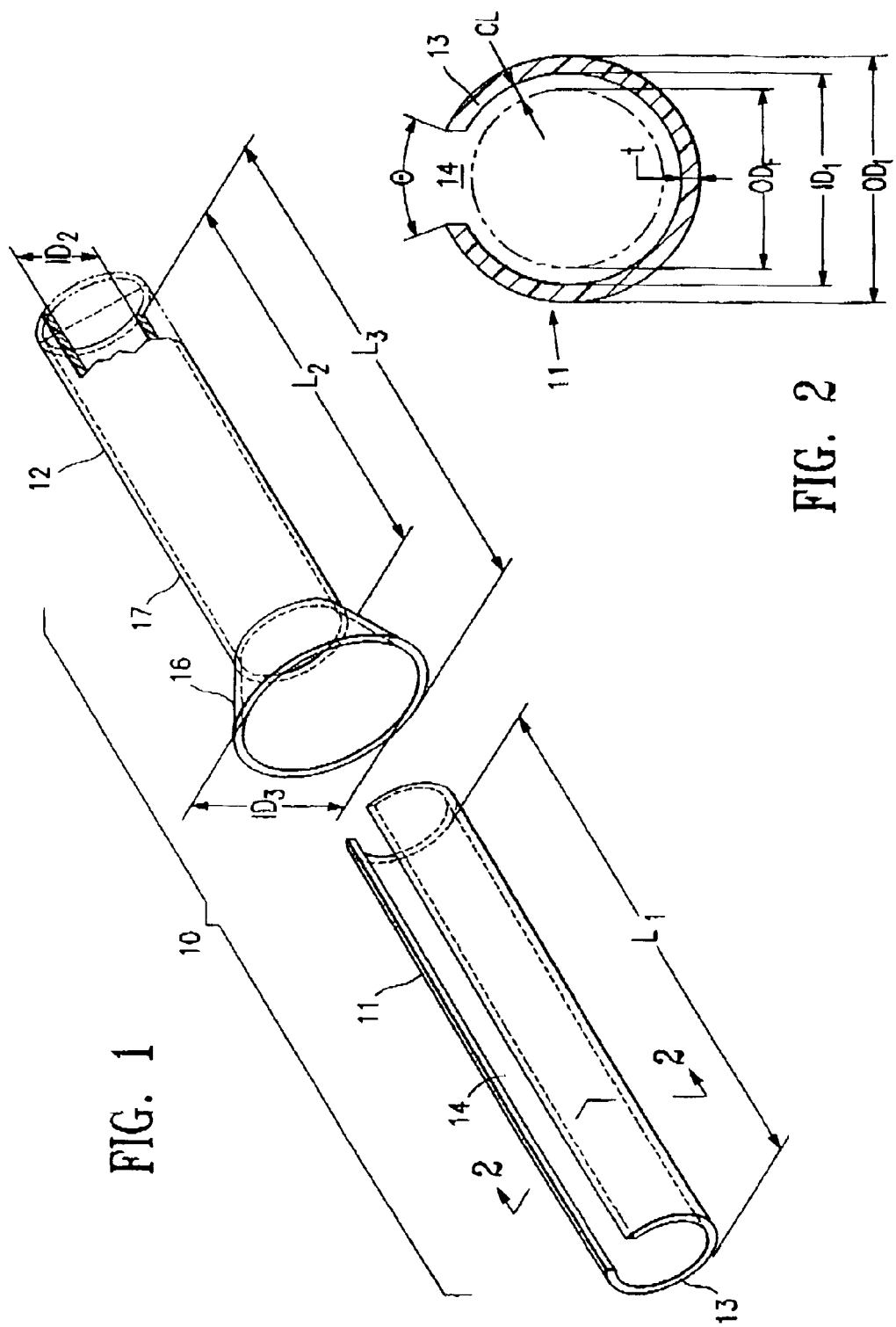

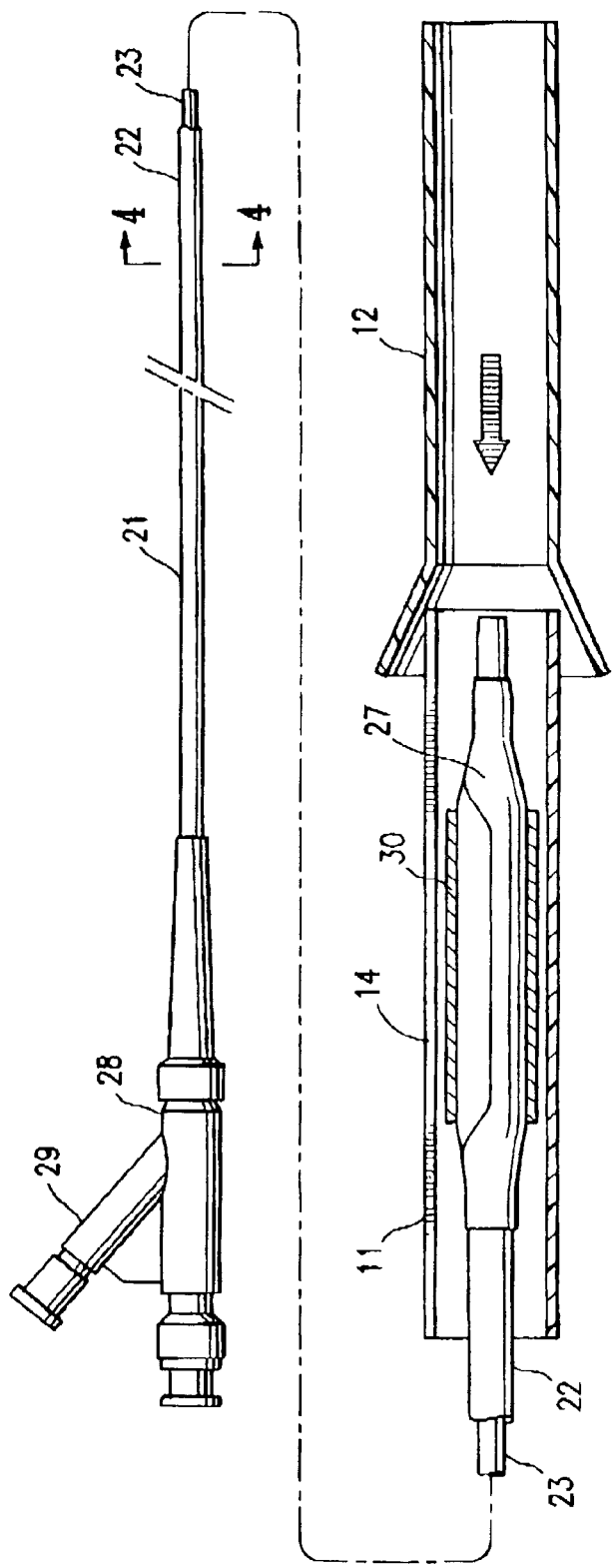
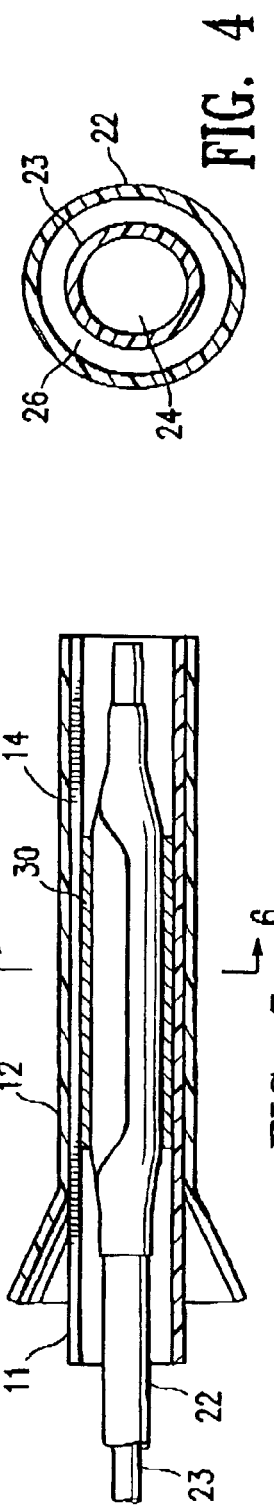
FIG. 3
FIG. 4
FIG. 5

PROTECTIVE SLEEVE ASSEMBLY FOR A BALLOON CATHETER

BACKGROUND OF THE INVENTION

This invention generally relates to catheters, and particularly protective sheaths for intravascular catheters for such as balloon catheters used in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. A tubular cover formed of synthetic or natural material may be present on an outer or inner surface of the stent. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

It is conventional practice to fold the deflated balloon about the tubular inner member of the catheter and then advance a protective sheath with an inner diameter larger than the outer diameter of the folded balloon over the folded balloon to hold the balloon in the folded condition for subsequent packaging and sterilization. In addition to protecting the balloon in storage and transit, the sheath holds the folded balloon in position so that, when sterilized at elevated temperatures, the balloon is heat set in the folded condition. A folded balloon presents a much smaller profile than an unfolded balloon and thus is more easily advanced through a patient's vascular system. Moreover, being heat set in the folded condition, the balloon returns in part to the folded condition when subjected to a vacuum after being inflated, such as when venting air from the interior of the balloon and catheter. To facilitate advancing the protective sheath over a folded balloon the sheath is frequently formed of a lubricous fluoropolymer material. Unfortunately, the fluoropolymer protective sheath is usually quite hard and it does not conform to the shape of the folded balloon, so care must be exercised in advancing the sheath over the folded balloon on the catheter and in subsequent handling so that the balloon is not damaged by the protective sheath.

Protective sheaths are described in numerous U.S. Patents, for example, U.S. Pat. No. 5,425,710 (Khair et al.), U.S. Pat. No. 5,033,007 (Euteneuer), U.S. Pat. No. 4,710,181 (Fuqua), U.S. Pat. No. 4,738,666 (Fuqua), U.S. Pat. No. 4,540,404 (Wolvek), U.S. Pat. No. 5,066,298 (Hess), U.S. Pat. No. 5,116,318 (Hillstead) and U.S. Pat. No. 5,417,707 (Parkola). All of the above references are incorporated herein by reference.

While there has been much development effort in protective sheaths for balloons and catheters, none of the sheaths heretofore developed have been completely satisfactory. These prior sheaths have been either very difficult to slide over or otherwise apply to a folded balloon, or they have been difficult to remove from the balloon before the catheter is inserted into the patient. The present invention provides a protective sheath which eliminates or minimizes the problems of these prior sheaths.

SUMMARY OF THE INVENTION

This invention is directed to a protector sleeve assembly for a balloon catheter, configured for being removably disposed on at least a section of the catheter and preferably on at least the catheter non-inflated balloon prior to introduction of the catheter in a patient's body lumen, including a radially collapsible inner sleeve, and an outer sleeve with a tapered section. The inner sleeve has a relaxed configuration with an inner diameter greater than the outer diameter of the noninflated balloon, and a radially collapsed configuration with an inner diameter less than the relaxed inner diameter of the inner sleeve. The outer sleeve is slidably positioned on at least a portion of the inner sleeve and has a tapered first section with an inner diameter tapering towards a nontapered second section, the nontapered second section having a substantially uniform inner diameter less than an outer diameter of the relaxed inner sleeve and configured to hold the inner sleeve in the collapsed configuration. Consequently, the inner sleeve is in the collapsed configuration with the outer sleeve nontapered portion thereon, and the inner sleeve is in the relaxed configuration with the outer sleeve removed therefrom. One aspect of the invention is directed to a method of sheathing a balloon catheter, including positioning an inner and outer sleeve of a protector sleeve assembly of the invention on the at least a section of a balloon catheter. The protector sleeve assembly of the invention provides improved sheathing of the catheter balloon, in which the protector sleeve assembly is securely and removably disposed on the balloon, and damage to the balloon from the application and subsequent removal of the sleeve assembly is prevented or minimized.

In a balloon catheter assembly of the invention having the protector sleeve assembly removably disposed on the catheter (e.g., on the catheter balloon) prior to introduction of the balloon catheter into a patient's body lumen, the balloon catheter generally includes an elongated shaft with at least one lumen therein, and a balloon on a distal shaft section with an interior in fluid communication with the shaft lumen.

The balloon has a length, a non-inflated configuration with an outer diameter for introduction into a the body lumen, and an inflated configuration. A variety of suitable balloon catheters can be used including dilatation, stent delivery, and/or drug delivery balloon catheters. The balloon is in a low profile, non-inflated configuration prior to introduction into the patient's body lumen, with the protector sleeve assembly thereon. A variety of suitable low profile, non-inflated configurations may be used depending on the nature of the balloon, including a deflated balloon with wings wrapped around the balloon, a balloon heat shrunk to a low profile non-expanded configuration, or a formed-in-place balloon which is not pre-expanded prior to inflation in the body lumen, as are conventionally known.

The inner sleeve is radially collapsible from the relaxed configuration to the collapsed configuration. In a presently preferred embodiment, the inner sleeve has a discontinuous cylindrical section formed by at least one cut-out region longitudinally extending along at least a portion of the sleeve. The terminology "cut-out region" should be understood to refer to a slot or gap in the sleeve, which is not necessarily formed by cutting the sleeve to form the slot/gap. The cut-out region may be formed by a variety of suitable methods including molding the sleeve with the cut-out region, or alternatively by removing material from the sleeve by any of a variety of suitable methods such as mechanically cutting, vaporizing, and laser removing the material. The relaxed inner sleeve collapses to the collapsed configuration as the edges of the sleeve defining the cut-out region are urged together by the outer sleeve being slid thereon (i.e., as the slot in the sleeve wall is forced to close). In a presently preferred embodiment, the inner sleeve collapses without portions of the inner sleeve overlapping one another, so that the collapsed inner sleeve has a uniform thickness cylindrical surface, thus producing a uniform radially inward force on the balloon, and producing a sheathed balloon having a uniformly round cross section. Thus, the edges defining the cut-out region come together preferably without overlapping one another in the collapsed configuration. However, a variety of suitable reversibly collapsible configurations can be used for the inner sleeve. For example, in another embodiment, the inner sleeve has a corrugated wall with longitudinally extending ridges formed by folds in the sleeve, so that the relaxed inner sleeve collapses as the ridges are urged together. Although discussed below primarily in terms of the embodiment of the inner sleeve having the cut-out region, it should be understood, a variety of suitable collapsing inner sleeve designs can alternatively be used. The relaxed inner sleeve is preferably configured to be slidably disposed over the noninflated balloon without touching the noninflated balloon (or a stent or other object on the noninflated balloon). Consequently, the relaxed inner sleeve can be slidably positioned over the noninflated balloon without rubbing against the balloon. Thus, the width of the cut-out section(s) is sufficiently large so that the inner sleeve collapses to the desired smaller inner diameter. In one embodiment in which the balloon has a stent mounted thereon, the width of the slot is not significantly greater than, and preferably less than the width of the stent struts, to thereby avoid catching or pinching the stent struts in the collapsing sections of the inner sleeve (e.g., within the cut-out region).

With the relaxed inner sleeve in position around the catheter balloon, the outer sleeve is slid onto the relaxed inner sleeve, tapered end first. The tapered section of the outer sleeve has at least a portion with a tapering inner diameter which is smaller than the relaxed outer diameter of the inner sleeve, so that the tapered section contacts the inner sleeve first as the outer sleeve is being slid thereon and causes the inner sleeve to collapse gradually as the tapered section of the outer sleeve is slid over the inner sleeve. The tapered section of the outer sleeve has a sufficiently long length and gradual taper that it gradually collapses the inner sleeve, and thus minimizes the force required to collapse the inner sleeve, and prevents or inhibits buckling of the inner sleeve as it collapses. In one embodiment, the length of the tapered section of the outer sleeve is about 10% to about 30% of the total length of the outer sleeve. In one embodiment, the inner and outer surface of the tapered section of the outer sleeve tapers at an angle of about 1 to about 5 degrees, preferably about 3 to about 4 degrees relative to the longitudinal axis of the outer sleeve. The nontapered section of the outer sleeve preferably has an inner diameter substantially equal to the collapsed outer diameter of the inner sleeve (i.e., within about ±0.05 mm of the inner sleeve collapsed outer diameter), so that the outer sleeve is slid onto the inner sleeve, to position the nontapered section at least along the section of the inner sleeve which is over the balloon, to hold the inner sleeve in the collapsed configuration on the balloon. Significantly, the longitudinal force required to slide the outer sleeve over the inner sleeve is not great enough to cause the inner sleeve to move longitudinally relative to the balloon (e.g., by buckling or compressing). Moreover, unlike sleeves which are applied and removed from a stent delivery balloon by twisting the sleeve on and off, the sleeve assembly of the invention does not induce twist that can be detrimental to stent deployment.

In a presently preferred embodiment, the outer sleeve is formed of a lubricious polymeric material or has a lubricious inner surface. Because the inner sleeve collapses radially onto the balloon, without having to be moved longitudinally relative to the balloon while in contact therewith, the inner sleeve does not have to be made of a lubricious material. The inner sleeve is preferably formed of a resilient polymeric material which self-expands to a diameter larger than the collapsed diameter when the collapsing force (i.e., the outer sleeve) is removed, such as polyethylene terephthalate (PET), high density polyethylene (HDPE), polytetrafluoroethylene (PTFE), or nylon. The preferred inner sleeve materials are nontacky, and may be lubricious as in the case of HDPE and PTFE, or nonlubricious as in the case of PET and nylon. In a presently referred embodiment, the inner sleeve material has a high modulus of about 80,000 psi or more, a high yield strength of about 3,000 psi or more, and a glass transition temperature which is above the processing temperatures of the catheter components to be sheathed.

The inner sleeve preferably has a length longer than the catheter balloon, so that the inner sleeve is disposed on at least the balloon and preferably on adjacent sections of the catheter shaft as well. The nontapered section of the outer sleeve preferably has a length not less than a working length of the balloon. In a presently preferred embodiment, the total length of the outer sleeve (i.e., tapered and nontapered sections) is less than the length of the inner sleeve, so that the operator can easily grasp the end of the inner sleeve down onto the catheter while sliding the outer sleeve over the inner sleeve. Consequently, the resistance caused by pushing the outer sleeve onto the inner sleeve does not cause the inner sleeve to slide and rub against the balloon.

The sleeve assembly of the invention can be used in a method of sheathing at least a section of a balloon catheter, as for example in a method of preparing a balloon catheter for storage, or during manufacture of the balloon catheter.

The inner sleeve in contact with the balloon is not caused to move longitudinally relative to the balloon during application or removal of the sleeve assembly from the balloon. Thus, the surface of the balloon is not rubbed. As a result, in a balloon catheter with a balloon or stent coated with a coating such as a drug or lubricious coating, the coating is not removed therefrom during the application or removal of the sleeve assembly of the invention. Moreover, long sections of the balloon catheter can be securely sheathed, which is particularly advantageous with long balloons, such as those of peripheral balloon catheters, where friction makes it difficult to slide a tight sheath over the entire balloon. These and other advantages of the invention will become more apparent from the following detailed description of the invention and the accompanying exemplary drawings.

BRIEF DESCRIPTION OF THE DRAWINGS

FIG. 1 is an elevational view of a protector sleeve assembly for a balloon catheter, embodying features of the invention, illustrating the outer sleeve and the inner sleeve before the outer sleeve is positioned thereon.

FIG. 2 is a transverse cross sectional view of the inner sleeve of the protector sleeve assembly shown in FIG. 1, taken along line 2—2.

FIG. 3 is an elevational, partially in section, view of a balloon catheter, during positioning of the outer sleeve on the inner sleeve on the catheter balloon.

FIG. 4 is a transverse cross sectional view of the balloon catheter shown in FIG. 3, taken along line 4—4.

FIG. 5 is an enlarged, partially in section, view of the distal end of the balloon catheter assembly shown in FIG. 4, after the outer sleeve has been positioned on the inner sleeve.

DETAILED DESCRIPTION OF THE INVENTION

Figure 7:
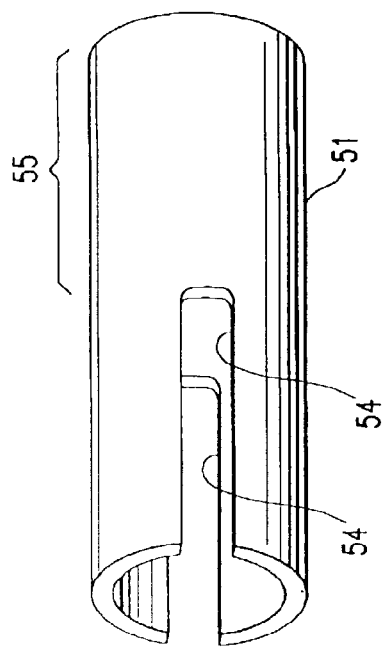
FIG. 7 is an elevational view of an alternative inner sleeve of a protector sleeve assembly embodying features of the invention, having multiple cut-out regions.

FIG. 1 illustrates a protector sleeve assembly 10 which embodies features of the invention, with an inner sleeve 11 and an outer sleeve 12. The inner sleeve 11 is illustrated in FIG. 1 in a relaxed configuration prior to being collapsed to a collapsed configuration by the force applied by the outer sleeve. The relaxed inner sleeve has a discontinuous cylindrical wall section 13 and a longitudinally extending cut-out region 14. The inner sleeve 11 has a length $L_1$, which is preferably longer than the length $L_3$ of the outer sleeve 12. The inner sleeve 11 is preferably formed of an injection molded polymeric tube formed of nylon, in which the cut-out region is formed during the molding process. The outer sleeve 12 has a tapered first section 16 and a nontapered second section 17. In the embodiment of FIG. 1, the tapered section 16 has an inner diameter $ID_3$ and an outer diameter tapering toward the nontapered section 17. The nontapered section 17 has an inner diameter $ID_2$ which is substantially uniform (varying within normal manufacturing tolerances) and which is less than the outer diameter of the relaxed inner sleeve and which is configured to hold the inner sleeve in the collapsed configuration. The inner sleeve 11 typically has a length of about 7 to about 9 cm, and the outer sleeve 12 typically has a length of about 4 cm to about 6 cm, although the sleeves 11, 12 may have a variety of suitable lengths generally depending on the length of the catheter balloon to be sheathed. The tapered section 16 of outer sleeve 12 typically has a length of about 0.5 to about 1 cm, and the nontapered section 17 typically has a length of about 3 to about 5 cm. The tapered section 16 length is preferably about 8% to about 30%, and more specifically about 10% to about 20%, of the total length of outer sleeve 12.

FIG. 2 illustrates a transverse cross sectional view of the inner sleeve 11 of FIG. 1, taken along line 2—2, with the collapsed configuration of the inner sleeve 11 shown in broken lines. The width of the cut-out region 14 is selected to provide a desired amount of decrease in the inner diameter of the inner sleeve 11 as the sleeve 11 collapses. Specifically, as illustrated in FIG. 2, where CL is the desired clearance between the inner sleeve 11 and the object being sleeved (e.g., a catheter balloon), it is the wall thickness of the inner sleeve 11, $OD_f$ is the outer diameter of the collapsed inner sleeve 11, $ID_1$ is the inner diameter of the relaxed inner sleeve 11, and $OD_1$ is the outer diameter of the relaxed inner sleeve 11, the angle (ø) formed by the cut out region 14 is equal to 720 $CL/(ID_f+2\ CL+2\ t)$.

In the embodiment of FIG. 1, the inner sleeve 11 has a single cut-out region 14. In one embodiment, the single cut-out region has a width which is about 5% to about 25%, preferably about 5% to about 15% of the circumference of the inner sleeve, and specifically which is about 0.5 mm to about 1 mm for an inner sleeve having a circumference of about 4 to about 9 mm. As a result the inner sleeve 11 in the relaxed configuration can be slidably disposed over the non-inflated balloon of a balloon catheter without touching the non-inflated balloon.

FIG. 3 illustrates an over-the-wire type balloon catheter 20 having a shaft 21 and an inflatable balloon 27 on a distal shaft section, with the inner sleeve 11 of the protector sleeve assembly 10 of FIG. 1 over the balloon 27 and with the outer sleeve 12 in position for sliding over the inner sleeve 11. Catheter 20 generally comprises elongated catheter shaft 21 having an outer tubular member 22 and an inner tubular member 23. Inner tubular member 23 defines a guidewire lumen 24 configured to slidingly receive a guidewire (not shown), and the coaxial relationship between outer tubular member 22 and inner tubular member 23 defines annular inflation lumen 26, as best shown in FIG. 4 illustrating a transverse cross section view of the distal end of the catheter shown in FIG. 3, taken along line 4—4. Inflatable balloon 27 disposed on a distal section of catheter shaft 21 has an elongated cylindrical expandable working section, a proximal skirt section sealingly secured to the distal end of outer tubular member 22 and a distal skirt section sealingly secured to the distal end of inner tubular member 23, so that its interior is in fluid communication with inflation lumen 26. An adapter 28 at the proximal end of catheter shaft 21 is configured to provide access to guidewire lumen 24 and to direct inflation fluid through arm 29 into inflation lumen 26. FIG. 3 illustrates the balloon 27 in a low profile, folded, tubular configuration prior to inflation, with a stent 30 mounted thereon for implanting in a patient's body lumen. In use, the distal end of catheter 20 is advanced to a desired region of the patient's body lumen in a conventional manner, and balloon 27 inflated to perform a procedure such as expanding the stent 30 into place in the body lumen, and the balloon deflated for removal of the catheter from the body lumen, leaving the stent 30 implanted therein.

FIG. 3 illustrates the inner sleeve 11 of the protector sleeve assembly 10 in the relaxed configuration before the outer sleeve 12 is slid thereon. The relaxed inner sleeve 11 has a larger inner diameter than the noninflated balloon 27. The inner sleeve covers a distal tip of the catheter, and extends from the distal tip to a location on the shaft 21 proximal to the balloon 27. The inner sleeve 11 has a length greater than the length of the outer sleeve 12 (and generally about 40% to about 75% greater than the length of outer sleeve 12), as best illustrated in FIG. 5 showing the assembly of FIG. 3 after the outer sleeve is slid onto the inner sleeve 11. Consequently, the proximal end of the inner sleeve 11 can be grasped down onto the shaft 21 as the outer sleeve 12 is slid proximally thereover, to facilitate positioning the outer sleeve 12 on the inner sleeve 11 without longitudinally sliding the collapsing/collapsed inner sleeve relative to the balloon catheter 20. The tapered section 16 of the outer sleeve 12 has a length and a taper angle such that it contacts the inner sleeve to increasingly collapse the inner sleeve 11 to the collapsed configuration as the outer sleeve is advanced thereover. After the tapered section 16 of the outer sleeve 12 is slid over the inner sleeve 11 to collapse the inner sleeve 11, the nontapered section 17 of the outer sleeve 12 is slidably advanced over the collapsed inner sleeve 11, to hold the inner sleeve 11 in the collapsed configuration. In a presently preferred embodiment, the outer sleeve 12 is formed of a lubricious material such as PTFE, to facilitate sliding the outer sleeve 12 over the inner sleeve 11.

In the embodiment illustrated in FIG. 5, the collapsed inner sleeve 11 is collapsed down onto the central working length of the non-inflated balloon 27 without compressing the non-inflated balloon and thus without decreasing the non-inflated balloon diameter, which is preferred in an embodiment in which the balloon catheter is a drug delivery balloon catheter with a drug coated on the balloon or with a drug delivery member mounted on the balloon. In one embodiment, the collapsed inner sleeve has an inner diameter about equal to the outer diameter of the non-inflated balloon 27, or the outer diameter of an assembly of the non-inflated balloon 27 with a drug delivery member mounted thereon. As a result, the collapsed inner sleeve 11 does not force the drug or other liquid out of the delivery member such as a drug coated stent or a drug impregnated tubular sheath on the balloon or stent.

Figure 6:
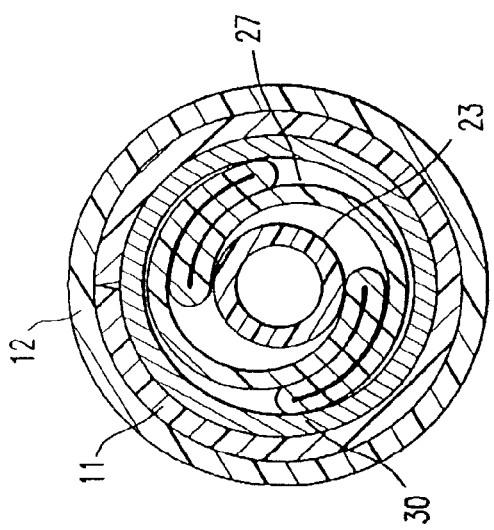
FIG. 6 is a transverse cross sectional view of the balloon catheter assembly shown in FIG. 5, taken along line 5—5.

As best illustrated in FIG. 6 showing a transverse cross section of the sleeved balloon catheter of the FIG. 5, taken along line 6—6, with the inner sleeve 11 in the collapsed configuration the cut-out region 14 is closed. In the embodiment illustrated in FIG. 6, the non-inflated balloon is in a folded configuration with deflated wings wrapped around the circumference of the balloon 27 and inner tubular member 23.

Prior to introduction of the balloon catheter in the patient's body lumen, the outer sleeve 12 is removed from the inner sleeve by distally sliding the outer sleeve 12 off the inner sleeve 11. The inner sleeve is preferably a resilient polymeric material, so that the inner sleeve 11 opens up to the relaxed configuration with the removal of the outer sleeve 12 therefrom. The relaxed inner sleeve is then removed from the balloon 27.

Figure 8:
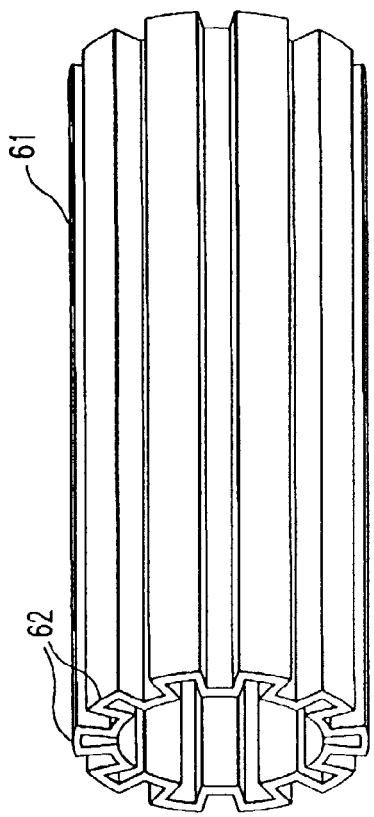
FIG. 8 is an elevational view of an alternative inner sleeve of a protector sleeve assembly embodying features of the invention, having a corrugated wall.

FIG. 7 illustrates an alternative embodiment of an inner sleeve 51 in a relaxed configuration, having multiple cut-out regions 54, and specifically in the embodiment of FIG. 7, two cut-out regions 54. The inner sleeve 51 has a continuous cylindrical section 55 so that the multiple cut-out regions 54 only extend part of the length of the inner sleeve 51. FIG. 8 illustrates an alternative embodiment of an inner sleeve 61 in a relaxed configuration, having a corrugated cylindrical wall with ridges 62 formed by folds in the sleeve wall. The ridges 62 are caused to come together to form the collapsed configuration, similar to the coming together of the edges defining the cut-out regions 54 in the embodiment of FIG. 7, when the outer sleeve 12 is slid thereon.

Figure 9:
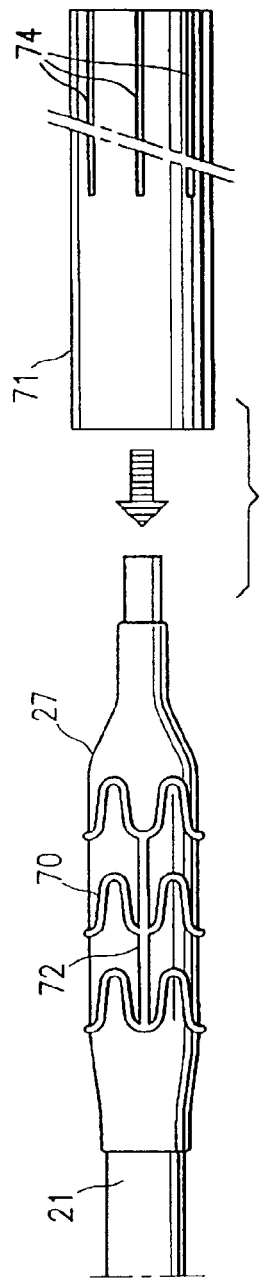
FIG. 9 is an elevational view of an inner sleeve having multiple cut-out regions, with the inner sleeve in position for sliding over a stent mounted on a catheter balloon.

In one embodiment having a stent mounted on the catheter balloon, the inner sleeve has one or more cut-out regions having a width sized relative to the stent struts to avoid catching the struts therein during collapse of the inner sleeve when the outer sleeve is slid thereon. In one embodiment, the multiple cut-out regions each have a width which is about 0% to about 50% larger than the width of the stent struts. FIG. 9 illustrates a stent 70 mounted on the non-inflated balloon 27 of the balloon catheter, with an inner sleeve 71 in the relaxed configuration in position for sliding over the balloon 27 and stent 70 thereon. The stent comprises interconnected stent struts 72, which may have a variety of suitable configurations as is conventionally known. The inner sleeve 71 has multiple cut-out regions 74 sized relative to the stent struts 72 to avoid catching the struts 72 therein during collapse of the inner sleeve 71 when the outer sleeve 12 (not shown in FIG. 9) is slid thereon. In the embodiment of FIG. 9, the inner sleeve 71 has multiple cut-out regions 74 each having a width less than the minimum width of the stent struts 72, so that the inner sleeve 71 radially collapses onto the balloon and stent thereon without catching a stent strut 72 in the cut-out region 74. In one embodiment, the multiple cut-out regions 74 each have a width which is about 1% to about 5% of the circumference of the inner sleeve, and specifically which is about 0.05 mm to about 0.5 mm for an inner sleeve having a circumference of about 4 mm to about 9 mm. Although the inner sleeve 71 is illustrated with more than two cut-out regions 74, it should be understood that the number of cut-out regions may vary and typically depends on characteristics such as the stent size, required clearance and final inner diameter of the inner sleeve. In a presently preferred embodiment, the inner sleeve 71 with multiple cut-out regions 74 has 2 to 8 cut-out regions each smaller than the stent struts 72.

To the extent not previously discussed herein, the various catheter components may be formed and joined by conventional materials and methods. For example, the outer and inner tubular members 22, 23 can be formed by conventional techniques, such as by extruding and necking materials found useful in intravascular catheters such as polyethylene, polyvinyl chloride, polyesters, polyamides, polyimides, polyurethanes, and composite materials.

The length of the balloon catheter 20 is generally about 108 to about 200 centimeters, preferably about 137 to about 145 centimeters, and typically about 140 centimeters for PTCA. The outer tubular member 22 has an outer diameter (OD) of about 0.017 to about 0.036 inch (0.43–0.91 mm), and an inner diameter (ID) of about 0.012 to about 0.035 inch (0.30–0.89 mm). The inner tubular member 23 has an OD of about 0.017 to about 0.026 inch (0.43–0.66 mm), and an ID of about 0.015 to about 0.018 inch (0.38–0.46 mm) depending on the diameter of the guidewire to be used with the catheter. The balloon 27 has a length of about 14 mm to about 110 mm, typically about 18 mm to about 30 mm, and an inflated working diameter of about 2 mm to about 25 mm, typically about 2.5 mm to about 4 mm.

While the present invention has been described herein in terms of certain preferred embodiments, those skilled in the art will recognize that modifications and improvements may be made without departing from the scope of the invention. For example, although the embodiment illustrated in FIG. 3 is an over-the-wire stent delivery catheter, the sleeve assembly of the invention may also be used with other types of intravascular catheters, such as rapid exchange balloon catheters. Rapid exchange catheters generally comprise a distal guidewire port in a distal end of the catheter, a proximal guidewire port in a distal shaft section located distally of the proximal end of the shaft and typically spaced a substantial distance from the proximal end of the catheter, and a short guidewire lumen extending between the proximal and distal guidewire ports in the distal section of the catheter. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter assembly, comprising:
   a) a balloon catheter having an elongated shaft with an inner lumen, and having a balloon on a distal shaft section with an interior in fluid communication with the inner lumen, the balloon having a length, an noninflated configuration with an outer diameter for introduction into a patient=s body lumen, and an inflated configuration;
   b) a drug delivery stent mounted on the balloon; and
   c) a protector sleeve assembly, removably disposed on at least the balloon and over the drug delivery stent prior to introduction of the catheter in the body lumen, comprising:
      i) an inner sleeve having a relaxed configuration with an inner diameter greater than the outer diameter of the noninflated balloon, and a radially collapsed configuration with an inner diameter less than the relaxed inner diameter, wherein an inner surface of the inner sleeve in the relaxed configuration is radially spaced apart from the noninflated balloon so that the inner sleeve can be positioned around the noninflated balloon without contacting the balloon or the drug delivery stent thereon; and
      ii) an outer sleeve on at least a portion of the inner sleeve, having a length, and a tapered first section with an inner diameter tapering towards a nontapered second section, the nontapered second section having a substantially uniform inner diameter less than an outer diameter of the relaxed inner sleeve and configured to hold the inner sleeve in the collapsed configuration, so that the inner sleeve is in the collapsed configuration with the outer sleeve nontapered section thereon and in the relaxed configuration with the outer sleeve removed therefrom, and so that the inner sleeve transforms from the relaxed configuration to the collapsed configuration without decreasing the diameter of the non-inflated balloon.

2. The balloon catheter assembly of claim 1 wherein the inner sleeve has a length greater than the length of the balloon.

3. The balloon catheter assembly of claim 1 wherein the outer sleeve has a length less than the length of the inner sleeve.

4. The balloon catheter of claim 1 wherein the tapered section has at least a portion with a tapering inner diameter which is smaller than the relaxed outer diameter of the inner sleeve.

5. The balloon catheter of claim 1 wherein the tapered section has an inner surface tapering at an angle of about 1 to about 5 degrees relative to a longitudinal axis of the outer sleeve.

6. The balloon catheter assembly of claim 1 wherein the relaxed inner diameter of the inner sleeve is at least about 5% to about 25% greater than the outer diameter of the noninflated balloon.

7. The balloon catheter assembly of claim 1 wherein the nontapered section of the outer sleeve has an inner diameter substantially equal to a collapsed outer diameter of the inner sleeve.

8. The balloon catheter assembly of claim 1 wherein the nontapered section of the outer sleeve has a length not less than a working length of the balloon.

9. The balloon catheter assembly of claim 1 wherein the tapered section of the outer sleeve has a length which is about 10% to about 33% of the length of the nontapered section of the outer sleeve.

10. The balloon catheter assembly of claim 1 wherein the inner sleeve is formed of a nonlubricious polymer selected from the group consisting of polyethylene terephthalate and nylon.

11. The balloon catheter assembly of claim 1 wherein the inner sleeve is formed of a lubricious polymer selected from the group consisting of polytetrafluoroethylene and high density polyethylene.

12. The balloon catheter assembly of claim 1 wherein the outer sleeve is formed of a lubricious polymer selected from the group consisting of polytetrafluoroethylene and high density polyethylene.

13. The balloon catheter assembly of claim 1 wherein the inner sleeve in the relaxed configuration has a discontinuous cylindrical wall section and at least one cut-out region longitudinally extending along at least part of the length of the sleeve, and the inner sleeve radially collapses as the cut-out region is closed.

14. The balloon catheter assembly of claim 13 wherein the inner sleeve has one cut-out region, and the single cut-out region has a width which is about 5% to about 15% of the circumference of the inner sleeve, so that the relaxed inner sleeve is configured to be slidably disposed over the noninflated balloon without touching the noninflated balloon.

15. The balloon catheter assembly of claim 13 wherein the inner sleeve has a continuous cylindrical section, so that the cut-out region extends only part of the length of the inner sleeve.

16. The balloon catheter assembly of claim 13 wherein the inner sleeve has multiple cut-out regions.

17. The balloon catheter assembly of claim 16 wherein each cut-out region has a width which is about 1% to about 5% of the circumference of the inner sleeve, so that the relaxed inner sleeve is configured to be slidably disposed over the noninflated balloon without touching the uninflated balloon.

18. The balloon catheter assembly of claim 16 wherein the stent comprises stent struts with a minimum width, and the multiple cut-out regions of the inner sleeve have a width less than the minimum width of the stent struts.

19. The balloon catheter assembly of claim 1 wherein the inner sleeve has a corrugated wall, and the inner sleeve radially collapses as the corrugations are brought together.

20. A protector sleeve assembly for a balloon catheter having a balloon with a non-inflated configuration and a drug delivery member mounted on the balloon or a drug delivery coating on the balloon, the protector sleeve assembly being configured for being removably disposed on the non-inflated balloon of the catheter prior to introduction of the catheter in a patient=s body lumen, and comprising:
   a) an inner sleeve having a relaxed configuration with an inner diameter, and a radially collapsed configuration with an inner diameter less than the relaxed inner diameter; and
   b) an outer sleeve on at least a portion of the inner sleeve, having a length, and a tapered first section with a tapering outer and inner diameter tapering towards a nontapered second section, the tapered first section having a length about 8% to about 30% of the length of the outer sleeve, and the nontapered second section having a substantially uniform inner diameter less than an outer diameter of the relaxed inner sleeve and configured to hold the inner sleeve in the collapsed configuration, so that the inner sleeve is in the collapsed configuration with the outer sleeve nontapered portion thereon and in the relaxed configuration with the outer sleeve removed therefrom, and so that the inner sleeve transforms from the relaxed configuration to the collapsed configuration without compressing the non-inflated balloon, such that the diameter of the non-inflated balloon is not decreased.

21. The protector sleeve assembly of claim 20 wherein the relaxed inner sleeve has a discontinuous outer surface formed by at least one cut-out region longitudinally extending along at least part of the length of the sleeve.

22. The protector sleeve assembly of claim 20 wherein the inner sleeve has a length greater than the length of the balloon.

23. The protector sleeve assembly of claim 20 wherein the outer sleeve has a length less than the length of the inner sleeve.

24. The protector sleeve assembly of claim 20 wherein the tapered section has an inner surface tapering at an angle of about 1 to about 5 degrees relative to a longitudinal axis of the outer sleeve.

25. The protector sleeve assembly of claim 20 wherein the inner sleeve has one cut-out region, and the single cut-out region has a width which is about 5% to about 15% of the circumference of the inner sleeve.

26. The protector sleeve assembly of claim 20 wherein the tapered section has at least a portion with a tapering inner diameter which is smaller than the relaxed outer diameter of the inner sleeve.

27. A method of sheathing a balloon catheter, comprising:
   a) positioning over a non-inflated balloon of a balloon catheter an inner sleeve having a length greater than the length of the non-inflated balloon, a relaxed configuration with an inner diameter greater than an outer diameter of the non-inflated balloon, and a collapsed configuration with an inner diameter less than the relaxed inner diameter, wherein an inner surface of the inner sleeve in the relaxed configuration is radially spaced apart from the non-inflated balloon so that the inner sleeve can be positioned around the non-inflated balloon without contacting the balloon; and
   b) providing an outer sleeve having a length, and a tapered first section with a tapering outer and inner diameter tapering towards a nontapered second section, the tapered first section having a length about 8% to about 30% of the length of the outer sleeve, and the nontapered second section having a substantially uniform inner diameter less than an outer diameter of the relaxed inner sleeve, and slidably advancing the outer sleeve over the inner sleeve so that the tapered section contacts the inner sleeve to increasingly collapse the inner sleeve to the collapsed configuration to transform the inner sleeve from the relaxed configuration to the collapsed configuration without decreasing the diameter of the non-inflated balloon, and slidably advancing the nontapered section of the outer sleeve over the inner sleeve to position the nontapered section over the collapsed inner sleeve to hold the inner sleeve in the collapsed configuration.

28. The method of claim 27 wherein the relaxed inner sleeve has a discontinuous outer surface formed by at least one cut-out region longitudinally extending along at least part of the length of the sleeve, so that collapsing the inner sleeve comprises closing the cut-out region.

29. The method of claim 28 wherein the inner sleeve has one cut-out region, and the single cut-out region has a width which is about 5% to about 15% of the circumference of the inner sleeve, and the inner sleeve in the relaxed configuration is longitudinally slid into position over the noninflated balloon without touching the non-inflated balloon.

30. The method of claim 28 wherein the balloon catheter is a stent delivery catheter having a stent mounted on the noninflated balloon under the inner sleeve, the stent comprising stent struts with a minimum width, and the multiple cut-out regions of the inner sleeve have a width less than the minimum width of the stent struts so that the inner sleeve collapses without catching the stent strut in the cut-out region.

31. The method of claim 27 wherein slidably advancing the outer sleeve over the inner sleeve comprises grasping a proximal end of the inner sleeve around the catheter and sliding the outer sleeve distally over the inner sleeve.

32. The method of claim 27 wherein the outer sleeve is advanced over the inner sleeve without moving the inner sleeve relative to the catheter.

33. The method of claim 27 wherein the inner sleeve is collapsed on the balloon without compressing the noninflated balloon.

34. The method of claim 27 further including, after (b), removing the outer sleeve from the balloon catheter, and allowing the inner sleeve to expand from the collapsed configuration to the relaxed configuration and removing the relaxed inner sleeve from the balloon catheter.

\* \* \* \* \*

UNITED STATES PATENT AND TRADEMARK OFFICE
CERTIFICATE OF CORRECTION

PATENT NO. : 7,105,013 B2
APPLICATION NO. : 10/261393
DATED : September 12, 2006
INVENTOR(S) : Jonathan P. Durcan It is certified that error appears in the above-identified patent and that said Letters Patent is hereby corrected as shown below:

Column 1,
Line 7, delete "for".

Column 6,
Line 28, delete "2 t" and insert --2t--.

Column 9,
Line 25, delete "an" and insert --a--.
Line 27, delete "patient=s" and insert --patient's--.

Column 11,
Line 2, delete "patient=s" and insert --patient's--.

Signed and Sealed this

Sixth Day of March, 2007

JON W. DUDAS
*Director of the United States Patent and Trademark Office*